(12) United States Patent
Trochesset et al.

(10) Patent No.: US 7,795,783 B2
(45) Date of Patent: Sep. 14, 2010

(54) TRANSDUCER ASSEMBLY

(75) Inventors: Wallace Trochesset, Friendswood, TX (US); Prakash Mistry, Sugar Land, TX (US); Peter E. Zasowski, Houston, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 1163 days.

(21) Appl. No.: 11/411,420

(22) Filed: Apr. 26, 2006

(65) Prior Publication Data

US 2007/0253582 A1 Nov. 1, 2007

(51) Int. Cl.
*H01L 41/08* (2006.01)
(52) U.S. Cl. .................. 310/334; 73/861.27; 73/861.28; 310/336
(58) Field of Classification Search ......... 310/334–337, 310/339
See application file for complete search history.

(56) References Cited

U.S. PATENT DOCUMENTS

| 4,649,754 | A | 3/1987 | Zacharias |
| 5,437,194 | A | 8/1995 | Lynnworth |
| 6,067,861 | A | 5/2000 | Shekarriz et al. |
| 6,268,683 | B1 * | 7/2001 | Li ............................ 310/348 |
| 6,378,357 | B1 | 4/2002 | Han et al. |
| 6,895,825 | B1 | 5/2005 | Barkhoudarian |

FOREIGN PATENT DOCUMENTS

| JP | 54-022096 A | 2/1979 |
| RU | 2041086 C1 | 8/1995 |
| RU | 2193164 | 11/2002 |
| RU | 2004122617 | 4/2008 |
| WO | 0050853 | 8/2000 |

OTHER PUBLICATIONS

European Search Report for European Application No. 07106608.8 mailed Jun. 24, 2008, 7 pages.
Examination Report in Indian Patent Application No. 884/CHE/2007 dated Feb. 18, 2010 (2 pages).
European Patent Office Communication in EP Application No. 07106608.8-2209/1850097, dated Feb. 23, 2009 (5 pages).
Office Action in Russian Patent Application No. 2007115725 dated Mar. 24, 2009 and partial English translation thereof (10 pages).
English Patent Abstract of RU2322695C2 from esp@cenet, published Apr. 20, 2008 (1 page).
English Patent Abstract of RU2193164C1 from esp@cenet, published Nov. 20, 2002 (1 page).
Office Action in Japanese Patent Application No. 2007112569 dated May 18, 2010 and partial English translation thereof (4 pages).

* cited by examiner

*Primary Examiner*—Mark Budd
(74) *Attorney, Agent, or Firm*—Osha Liang LLP

(57) ABSTRACT

Transducer assemblies and methods of replacing having a housing, a removable diaphragm, and a sealing diaphragm. The transducer assembly may be used with a spool piece to prevent fluid from escaping from the spool piece when parts of the transducer assembly are removed.

18 Claims, 3 Drawing Sheets

TRANSDUCER ASSEMBLY

BACKGROUND OF INVENTION

1. Field of the Invention

The present invention relates generally to devices used to measure fluid flow. Specifically, embodiments of the present invention generally relate to a transducer assembly that uses ultrasonic signals to measure fluid flow and predict a flow profile of a fluid.

2. Background Art

In industries involving fluid flow, accurate measurements of fluid flow rates are often very important and, thereby, may be required. For example, in the oil and gas industry, accurate flow rate measurements are needed for leak detection, process control applications, and custody transfer (e.g. the transfer of ownership of oil and gas at a crude oil loading and off-loading station). Conventional flow measurement technologies include turbine flow meters and positive displacement flow meters. Recently though, ultrasonic meters have been gaining popularity in the oil and gas industry due to their advantages over conventional technologies. These advantages include: excellent long-term reproducibility, less sensitivity to fluid properties such as viscosity and pressure, better open-box accuracy, wider range of linearity, and lower cost of maintenance due to the fact that no moving parts are used in these ultrasonic meters.

In typical operation, an ultrasonic flow meter uses a transducer to transmit an ultrasonic signal into a fluid that is received by a second transducer. The fluid carrying the wave of the ultrasonic signal alters the wave's frequency (Doppler effect) and transit-time (velocity superposition), such that a measure of one of these two quantities may be used to determine a fluid flow rate. Based on these principles, two major ultrasonic flow measurement technologies exist: Doppler and transit-time. The majority of the methods developed to measure fluid flow profiles have been based upon Doppler technology (e.g. U.S. Pat. Nos. 6,067,861 and 6,378,357). However, Doppler signals rely heavily on particle size and concentration of particles, both characteristics of fluid that may vary, thereby leading to poor accuracy and repeatability. Thus, for purposes of accuracy, the oil and gas industry prefers the use of transit-time meters.

The principles of transit-time ultrasonic meters are well established. Referring to FIG. 1, a spool piece 101 is shown with a pair of transducers 111 and 113 for ultrasonic transit-time measurement. In some configurations, transducers may be clamped on the outside wall of a spool piece. However, in FIG. 1, the transducers 111 and 113 are installed in a wall 103 of the spool piece 101 (referred to as "wetted" transducers). This enables the "wetted" transducers 111 and 113 to have better sensitivity. The transducers 111 and 113 are capable of transmitting and receiving ultrasonic signals. Arrow F indicates flow direction of fluid through the spool piece 101, a line L refers to a path length of the ultrasonic signal between the transducers 111 and 113, θ refers to an angle between the path length L of the ultrasonic signal and the flow direction F, $t_u$ refers to a transit-time of the ultrasonic signal upstream (an ultrasonic signal from transducer 113 to transducer 111) along line L, and $t_d$ refers to a transit-time of the ultrasonic signal downstream (an ultrasonic signal from transducer 111 to transducer 113) along line L. With these variables, a velocity V of the flow F of the fluid along the path length L may found, as shown below in equation [1]:

$$V = \frac{L}{2\cos\theta} \cdot \frac{t_u - t_d}{t_u \cdot t_d} \qquad \text{Equation [1]}$$

Multiple pairs of transducers may be used in a similar configuration to the transducers 111 and 113 in FIG. 1 to determine an fluid flow rate and/or fluid flow profile through a spool piece. Such a configuration is commonly referred to as a "multi-path" ultrasonic transit-time flow meter.

One issue with these wetted transducers is that when maintenance is required and the transducers need to be replaced, they are not readily accessible. For example, when a wetted transducer needs to be replaced, fluid flow may need to be stopped to prevent fluid from leaking through an opening within the spool piece the wetted transducer is installed. Further, the spool piece with the installed transducer may even need to be taken out of the pipe line to enable access to the transducer. Depending on the complexity of the design of the spool piece and the pipe line, the replacement and maintenance of the transducer may lead to the loss of many valuable hours in downtime. Thus, as shown, what is still needed is improved transducers and methods for easier replacement without sacrificing accuracy in measurements of the fluid.

SUMMARY OF INVENTION

In one aspect, the present invention relates to a transducer assembly. The transducer assembly includes a housing, a sealing diaphragm, a removable diaphragm, and a piezoelectric crystal. The removable diaphragm is radially constrained to the housing and biased towards the sealing diaphragm, and the piezoelectric crystal is disposed within the removable diaphragm.

In another aspect, the present invention relates to a spool piece. The spool piece includes a transducer assembly disposed within the spool piece. The transducer assembly includes a housing at least partially disposed within a wall of the spool piece, a sealing diaphragm disposed within the wall of the spool piece, and a removable diaphragm radially constrained to the housing and disposed within the wall of the spool piece. A piezoelectric crystal is disposed within the removable diaphragm and the removable diaphragm is biased towards the sealing diaphragm.

In another aspect, the present invention relates to a method of replacing a transducer assembly from a spool piece. The transducer assembly includes a housing, a removable diaphragm, and a sealing diaphragm. The method includes removing the housing and the removable diaphragm from an opening of the spool piece and preventing fluid from escaping within the spool piece with the sealing diaphragm while the housing and the removable diaphragm are removed from the opening of the spool piece.

Other aspects and advantages of the invention will be apparent from the following description and the appended claims.

DETAILED DESCRIPTION

In one aspect, embodiments of the present invention generally relate to an improved transducer assembly. More specifically, one or more embodiments of the present invention may provide a transducer assembly including at least two diaphragms and a piezoelectric crystal to measure transit-time of ultrasonic signals.

Figure 1:
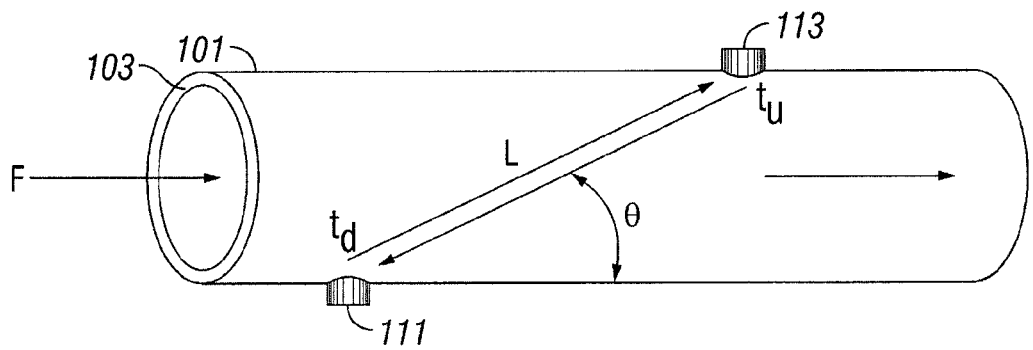
FIG. 1 shows a prior art spool piece with transducers for ultrasonic transit-time measurements.
Figure 2:
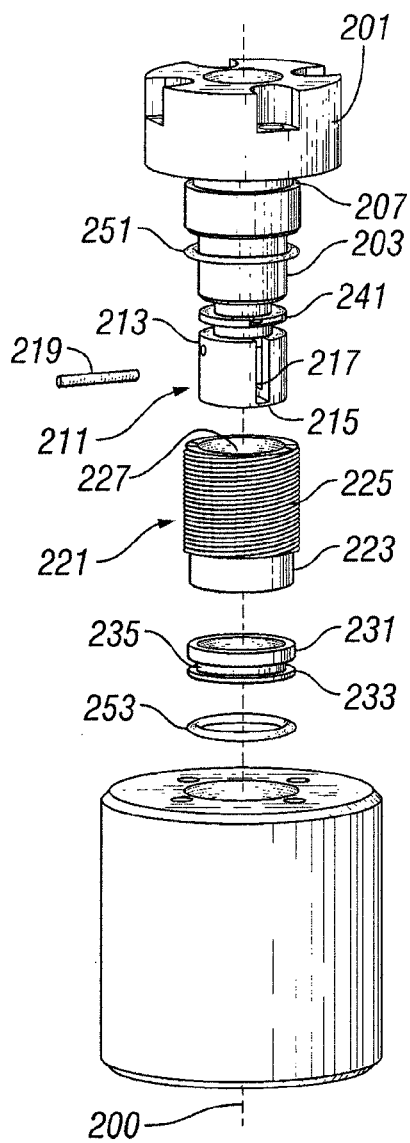
FIG. 2 shows a transducer assembly in accordance with an embodiment of the present invention.

FIG. 2 shows an exploded view of a transducer assembly in accordance with an embodiment of the present invention. The transducer assembly is disposed about an axis 200 and includes a housing 201 with a removable diaphragm 211. The removable diaphragm 211 includes a cylinder wall 213 having a disc 215 attached to an end of the cylinder wall 213. Further, a piezoelectric crystal 217 is disposed within the removable diaphragm 211. Specifically, the piezoelectric crystal 217 may be located inside the removable diaphragm 211 and secured to the disc 215. The piezoelectric crystal will be discussed with more detail below.

Referring still to FIG. 2, the removable diaphragm 211 may be radially constrained to the housing 201. As used herein, "radially" constrained refers to the removable diaphragm being restricted in radial movement with respect to the axis of the housing. In this embodiment, the removable diaphragm 211 is radially constrained to an end 203 of the housing 201 by being disposed about an outside of the end 203 of the housing 201. However, in another embodiment, the removable diaphragm 211 may be radially constrained to the housing 201 by being disposed within the housing 201, for example being disposed within an inside of the end 203 of the housing 201.

Figure 3:
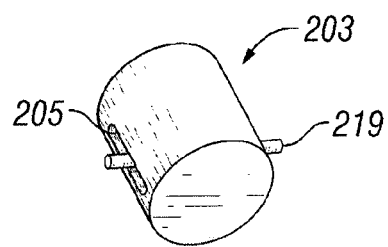
FIG. 3 shows a recess in the end of the housing of the transducer assembly in accordance with an embodiment of the present invention.

Further, referring still to FIG. 2, the removable diaphragm 211 may be rotationally constrained to the housing 201. As used herein, "rotationally" constrained refers to the removable diaphragm being restricted in rotational movement with respect to the axis of the housing. In this embodiment, the removable diaphragm 211 is rotationally constrained to the housing 201 with a pin 219. The end 203 of the housing 201 may have a recess 205 (shown in FIG. 3) that is the width of the pin 219 and runs along the length of the end 203 of the housing 201. The pin 219 may then fit into the recess 205 and be capable of moving axially (along the axis 200) within the recess 205, but would be constrained by the recess 205 from rotating about the axis 200. The pin 219 may then be secured to the cylinder wall 213 of the removable diaphragm 211, thereby enabling the removable diaphragm 211 to be rotationally constrained to the housing 201.

Referring still to FIG. 2, the transducer assembly may further include a sleeve 221 and a sealing diaphragm 231. The sealing diaphragm 231 includes a disc 233 and may be located at an end 223 of the sleeve 221. As shown in this embodiment, the sealing diaphragm 231 may be disposed about an outside of the end 223 of the sleeve 221. The sleeve 221 may include a through hole 227. The through hole 227 may form a generally cylindrical passage, as shown. Preferably, the through hole 227 is large enough to enable the removable diaphragm 211 and the end 203 of the housing 201 to be disposed within the sleeve 221. The sleeve 221 may further include a threaded portion 225 to enable the sleeve 221 to threadedly engage with a spool piece (not shown here).

Referring still to FIG. 2, the transducer assembly may further include a biasing mechanism 241. In this embodiment, the biasing mechanism 241 is a spring. However, those having ordinary skill in the art will appreciate the other biasing mechanisms may be used without departing from the scope of the present invention. Regardless, the biasing mechanism 241 may be disposed about the housing 201, specifically the end 203 of the housing 201, such that the biasing mechanism 241 may be used to bias the removable diaphragm 211 (together with the piezoelectric crystal 217) towards the sealing diaphragm 231. This bias may be used to ensure contact between the removable diaphragm 211 and the sealing diaphragm 231 and, hence, better sensitivity for the transducer assembly. The biasing mechanism 241 may be radially constrained to the housing 201. Specifically, the biasing mechanism 241 may be disposed about the housing 201, thereby inhibiting any radial movement inwards of the biasing mechanism 241 with respect to the axis 200 of the housing 201, and the biasing mechanism 241 may be disposed within the sleeve 221 with the removable diaphragm 211 and the end 203 of the housing 201, thereby inhibiting any radial movement outwards of the biasing mechanism 241 with respect to the axis 200 of the housing 201. Thus, the biasing mechanism 241 may only be capable of moving along the axis 200 of the housing 201 when radially constrained to the housing 201 or the sleeve 221.

Referring still to FIG. 2, a groove 207 may be formed in the end 203 of the housing 201. The groove 207 may be used to fit a seal 251 about the housing 201. The seal 251, which may be an o-ring as shown, may be used to provide a seal between the housing 201 and the sleeve 221 when the end 203 of the housing 201 is disposed within the sleeve 221. Similarly, a groove 235 may be formed in the sealing diaphragm 231. The groove 235 may be used to fit a seal 253 about the sealing diaphragm 231. The seal 253, which may also be an o-ring as shown, may be used to provide a seal between the sealing diaphragm 231 and a spool piece (not shown here).

Figure 4:
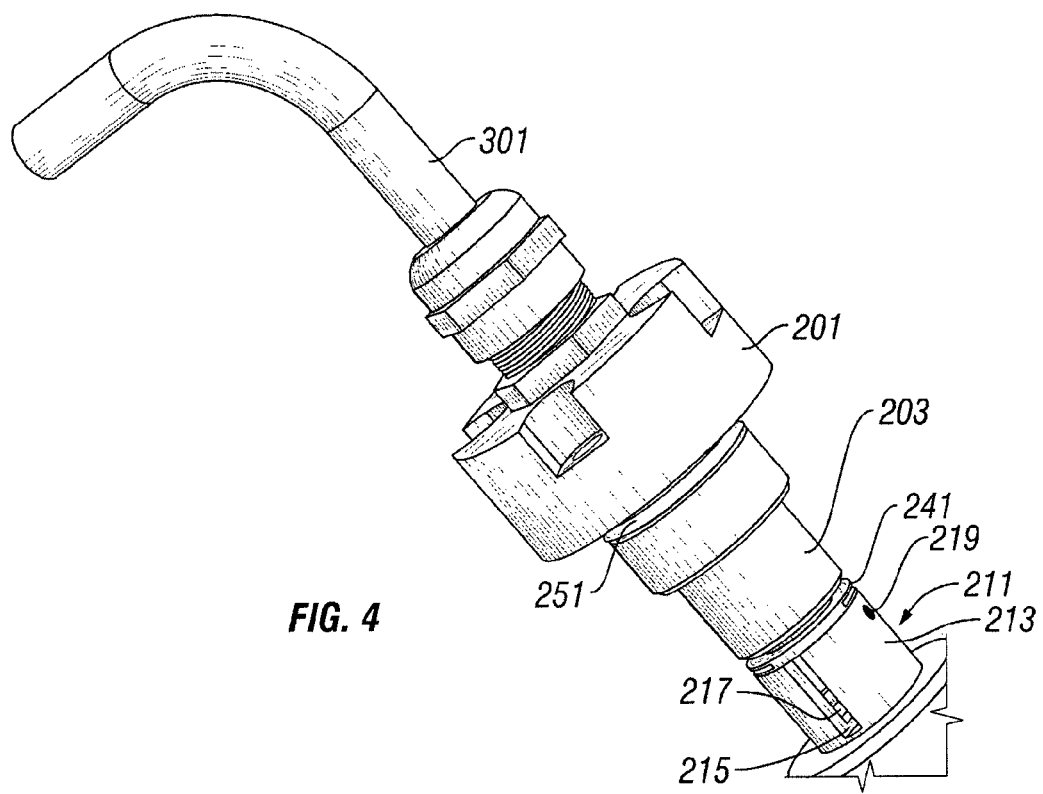
FIG. 4 shows a transducer assembly connected to an electrical energy source in accordance with an embodiment of the present invention.

FIG. 4 shows a transducer assembly in accordance with an embodiment of the present invention. In this embodiment, the piezoelectric crystal 217 is connected to an electrical energy source (not shown), such as a battery, through a wire 301. Piezoelectric crystals may be used to convert electrical energy into mechanical energy or be used to convert mechanical energy into electrical energy. For example, in one embodiment, electrical charges may be sent from the electrical energy source through the wire 301 to the piezoelectric crystal 217. The electrical charges may then be converted by the piezoelectric crystal 217 into acoustic energy (e.g. mechanical energy) such that an acoustic signal may be produced. Reversibly, in another embodiment, mechanical energy, for example from an acoustic signal, may be received by the piezoelectric crystal 217. This mechanical energy may then be converted by the piezoelectric crystal 217 into electrical energy. The electrical energy may then be sent by the piezoelectric crystal 217 through the wire 301.

The piezoelectric crystal may be comprised of many materials, ceramics and quartz crystals being most common. Specifically, in one embodiment, the piezoelectric crystal may be comprised of Kézite K600, available from Keramos of Piezo Technologies, which is a modified lead zirconate titanate piezoelectric ceramic. The material of the piezoelectric crystal may then be modified in various ways to produce different wave modes of the acoustic signal. For example, the overall shape of the piezoelectric crystal determines a sound field of the acoustic signal produced from the piezoelectric crystal.

Figure 5:
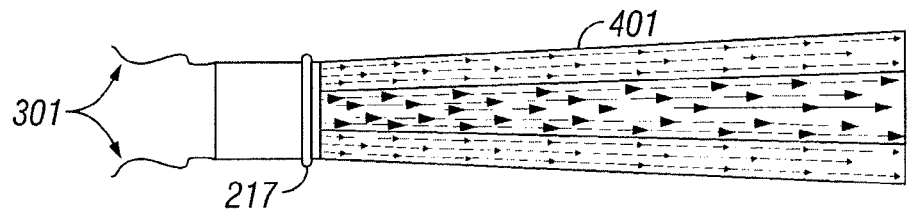
FIG. 5 shows a sound field of a piezoelectric crystal in accordance with an embodiment of the present invention.

FIG. 5 shows an example of a sound field 401 produced by the piezoelectric crystal 217 in accordance with an embodiment of the present invention. In this embodiment, the piezoelectric crystal 217 is in the shape of a cylindrical disc and produces the sound field 401, as shown, when receiving electrical charges through the wire 301. Further, the thickness of the piezoelectric crystal may determine the frequency of the acoustic energy produced by the piezoelectric crystal. Specifically, the piezoelectric crystal produces a wavelength about twice its thickness. In one embodiment, the piezoelectric crystal is capable of producing an ultrasonic signal, preferably ranging in frequencies from 0.8 MHz to 1.2 MHz.

Figure 6:
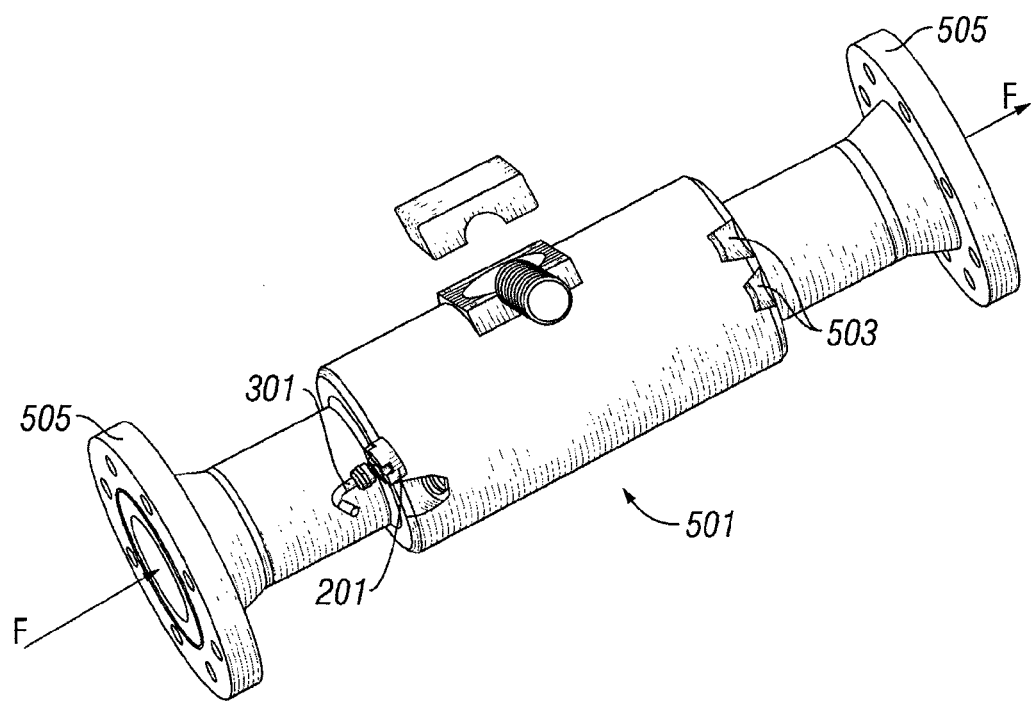
FIG. 6 shows a spool piece with a transducer assembly in accordance with an embodiment of the present invention.

Referring now to FIG. 6, a spool piece 501 with a transducer assembly in accordance with an embodiment of the present invention is shown. The spool piece 501 includes openings 503 that may receive transducer assemblies, such as the transducer assembly shown in FIG. 2. For example, in one embodiment, the threaded portion 225 of the sleeve 221 of the transducer assembly may threadedly engage with an opening 503 in the spool piece 503. This would enable the sleeve 221 and the attached sealing diaphragm 231 to be secured within the spool piece 501. The end 203 of the housing 201 and the removable diaphragm 211 may be disposed within the sleeve 221. Because the transducer assembly may be disposed within the spool piece 501, as shown, the transducer assembly may be a wetted transducer.

Referring still to FIG. 6, the spool piece 501 may then be installed in a pipe line (not shown) through the use of flanges 505. When in the pipe line, fluid may flow (arrow F indicating direction of fluid flow) through the spool piece 501, in which transducer assemblies may be used to measure fluid flow through the spool piece 501. In one embodiment, the transducer assembly secured within the spool piece 501 shown in FIG. 6 may be paired with a corresponding transducer assembly (not shown) installed on the opposite side of the spool piece 501 and be downstream of the shown transducer assembly. The transducer assembly shown in FIG. 6 will be referred to as the "upstream" transducer assembly, and the transducer assembly not shown on the opposite side of the spool piece 501 will be referred to as the "downstream" transducer assembly. In one embodiment, the upstream and downstream transducer assemblies may be capable of sending and receiving ultrasonic signals to each other. Transit-time of the signals between the transducer assemblies may be used in Equation [1], for example, to determine velocity of the fluid flow F along a path length between the upstream and downstream transducer assemblies. In another embodiment, the spool piece 501 may have multiple pairs of upstream and downstream transducer assemblies secured within the openings 503 to be a multi-path ultrasonic transit-time flow meter. Embodiments of the present invention may then be used to determine fluid flow rate and/or the fluid flow profile through the spool piece and pipeline.

Following a method in accordance with an embodiment of the present invention, a transducer assembly may be replaced from a spool piece. A transducer assembly in accordance with an embodiment of the present invention may be replaced without interfering with the fluid flow through the spool piece. For example, if the piezoelectric crystal 217 needs to be replaced within the transducer assembly, the housing 201 may be removed from the sleeve 221. The sleeve 221 may be secured to the spool piece 501, for example, through a threaded engagement with the threaded portion 225 of the sleeve 221. Because of this, the housing 201 may be removed from the opening 503 of the spool piece 501, but the sleeve 221 may remain secured within the opening 503 of the spool piece 501. When the housing 201 is removed from the spool piece 501, the removable diaphragm 211 and the biasing mechanism 241, both which may be constrained to the housing 201, may be removed also. With the housing 201 and the removable diaphragm 211 removed from the spool piece 501, the removable diaphragm 211 may be replaced and/or the piezoelectric crystal 217 may be replaced. During this replacement, the sealing diaphragm 231, which may be disposed about the end 223 of the sleeve 221 and may be in direct contact with the fluid within the spool piece 501, may remain secured within the opening 503 of the spool piece 501. In this manner, the sealing diaphragm 231 may prevent any fluid escaping from the spool piece 501 during replacement of the removable diaphragm 211, for example.

Further, following another method in accordance with an embodiment of the present invention, the sealing diaphragm of the transducer assembly may be replaced without having to take the spool piece out of the pipe line. For example, if the sealing diaphragm 231 needs to be replaced, the sleeve 221 may be removed from the opening 503 of the spool piece 501. The sealing diaphragm 231, which may be disposed about the end 223 of the sleeve 221, may be removed also. The sealing diaphragm 231 may then be replaced while out of the spool piece 501. Because the sealing diaphragm 231 will be removed from the opening 503 of the spool piece 501, fluid may escape from the spool piece 501. To prevent fluid from escaping from the spool piece 501, fluid flow F may need to be stopped through the spool piece 501, but the replacement of the sealing diaphragm 231 does not necessitate taking the spool piece 501 out of the pipe line (not shown).

Preferably, the removable diaphragm and the sealing diaphragm are comprised of plastic. Specifically, the removable diaphragm and the sealing diaphragm may be comprised of Ultem 1000, a thermoplastic polyetherimide high heat polymer available from General Electric. Further, the discs of the removable diaphragm and the sealing diaphragm may be relatively thin, preferably ranging from within about 1-3 mm (0.04-0.12 in) in thickness. Further, the piezoelectric crystal may be secured to the disc of the removable diaphragm with the use of an adhesive, preferably a viscous adhesive. With the diaphragms being comprised of plastic, their discs being relatively thin, and/or the use of a viscous adhesive when securing the piezoelectric crystal, this may allow a better signal (i.e. prevent or limit loss of strength of signal) to be sent and received by the transducer assembly.

Those having ordinary skill in the art will appreciate that embodiments of the present invention may have one or more of the following advantages. Typically, in the prior art, when replacing the transducer assembly or components of the transducer assembly, especially wetted transducers, fluid flow through the pipe line or spool piece may be stopped to prevent fluid from escaping through the openings that the transducers may be secured within. However, with the present invention, the fluid flow may not have to be interfered with because the sealing diaphragm may be used to prevent any fluid from escaping from the spool piece.

Further, a transducer assembly in accordance with one or more embodiments of the present invention may be "intrinsically safe" and/or zone 0 certified. An intrinsically safe device is a device incapable of causing ignition of flammable material under normal use or under any fault conditions likely to occur in practice. Zone 0 refers to an atmosphere that always has explosive material, such as explosive gas, present. Embodiments of the present invention may be intrinsically safe and zone 0 certified, thereby enabling the transducer assembly to be used safely in extremely explosive atmospheres, such as atmospheres common to the oil and gas industry.

Further, the use of a biasing mechanism in a transducer assembly in accordance with one or more embodiments of the present invention may allow a better signal (i.e. prevent or limit loss of strength of signal) to be sent and received by the transducer assembly. When end of the housing and the removable diaphragm are disposed within the sleeve of the transducer assembly, the biasing mechanism may bias the removable diaphragm towards the sealing diaphragm. This may enable the removable diaphragm and the piezoelectric crystal disposed therein to have a tight contact with the sealing diaphragm, enabling a better signal transfer through the transducer assembly.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A transducer assembly, comprising:
   a housing;
   a sealing diaphragm;
   a removable diaphragm radially constrained to the housing;
   a piezoelectric crystal disposed within the removable diaphragm; and
   a sleeve;
   wherein the sealing diaphragm is located at an end of the sleeve;
   wherein the removable diaphragm and at least a portion of the housing are disposed within the sleeve; and
   wherein the removable diaphragm is biased towards the sealing diaphragm.

2. The transducer assembly of claim 1, wherein the sleeve comprises a threaded portion.

3. The transducer assembly of claim 1, further comprising a biasing mechanism disposed about the housing to bias the removable diaphragm towards the sealing diaphragm.

4. The housing assembly of claim 3, wherein the biasing mechanism is radially constrained to the housing.

5. The transducer assembly of claim 1, wherein the transducer assembly is configured to be disposed on a spool piece.

6. The transducer assembly of claim 1, further comprising:
   a sealing element disposed about the housing, wherein the sealing element provides a seal between the sleeve and the housing.

7. The transducer assembly of claim 5, further comprising:
   a sealing element disposed about the sealing diaphragm, wherein the sealing element provides a seal between the sealing diaphragm and the spool piece.

8. The transducer assembly of claim 1, wherein the piezoelectric crystal is secured to the removable diaphragm with an adhesive.

9. The transducer assembly of claim 1, wherein the transducer assembly is intrinsically safe.

10. The transducer assembly of claim 1, wherein the transducer assembly is zone 0 certified.

11. A spool piece used to measure flow of a fluid, the spool piece comprising:
    a transducer assembly disposed on the spool piece,
    wherein the transducer assembly comprises:
      a housing at least partially disposed within a wall of the spool piece;
      a sealing diaphragm disposed within the wall of the spool piece;
      a removable diaphragm radially constrained to the housing and disposed within the wall of the spool piece;
      a piezoelectric crystal disposed on the removable diaphragm; and
      a sleeve;
      wherein the removable diaphragm is disposed within the sleeve;
      wherein at least a portion of the housing is disposed within the sleeve; and
      wherein the removable diaphragm is biased towards the sealing diaphragm.

12. The spool piece of claim 11, wherein the sleeve threadedly engages with the spool piece.

13. The spool piece of claim 11, further comprising a biasing mechanism disposed about the housing to bias the removable diaphragm towards the sealing diaphragm.

14. A method of replacing a transducer assembly from a spool piece, the method comprising:
    providing the transducer assembly having a housing, a removable diaphragm, a sleeve with the removable diaphragm and at least a portion of the housing disposed within the sleeve, a sealing diaphragm located at an end of the sleeve, and a biasing mechanism disposed about the housing and biasing the removable diaphragm towards the sealing diaphragm;
    removing the housing and the removable diaphragm from an opening of the spool piece; and
    preventing fluid from escaping within the spool piece with the sealing diaphragm while the housing and the removable diaphragm are removed from the opening of the spool piece.

15. The method of claim 14, wherein a piezoelectric crystal is disposed within the removable diaphragm.

16. The method of claim 14, further comprising:
    replacing the removable diaphragm; and
    inserting the housing and the removable diaphragm into the opening of the spool piece.

17. The method of claim 14, wherein the sleeve comprises a threaded portion and threadedly engages with the spool piece.

18. The method of claim 14, wherein the biasing mechanism is radially constrained to the housing.

* * * * *